(12) United States Patent
Guenther et al.

(10) Patent No.: US 8,618,200 B2
(45) Date of Patent: Dec. 31, 2013

(54) ELECTRODE LEAD FOR MEDICAL USE, INSULATING TUBE AND METHOD FOR PRODUCING THE SAME

(75) Inventors: Thomas Guenther, Michendorf (DE); Gernot Kolberg, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 11 days.

(21) Appl. No.: 13/170,840

(22) Filed: Jun. 28, 2011

(65) Prior Publication Data
US 2012/0022624 A1    Jan. 26, 2012

Related U.S. Application Data

(60) Provisional application No. 61/366,529, filed on Jul. 22, 2010.

(51) Int. Cl.
*C08K 3/10*      (2006.01)
(52) U.S. Cl.
USPC ......... 524/403; 607/115; 428/36.4; 428/35.8; 428/36.1; 264/299; 264/209.1
(58) Field of Classification Search
USPC ........................................................ 524/403
See application file for complete search history.

(56) References Cited

U.S. PATENT DOCUMENTS

| | | | |
|---|---|---|---|
| 5,016,646 A * | 5/1991 | Gotthardt et al. | 607/122 |
| 5,767,183 A * | 6/1998 | Takei et al. | 524/430 |
| 6,078,839 A | 6/2000 | Carson | |
| 7,514,095 B2 * | 4/2009 | Nelson et al. | 424/426 |
| 2005/0137664 A1 | 6/2005 | Sommer et al. | |
| 2008/0033522 A1 * | 2/2008 | Grewe et al. | 623/1.11 |
| 2009/0210043 A1 | 8/2009 | Reddy | |
| 2011/0112614 A1 | 5/2011 | Haarer | |

FOREIGN PATENT DOCUMENTS

WO     WO 93/20750     * 10/1993

OTHER PUBLICATIONS

European Search Report and Notes to the European Search Report on European Patent Application No. EP 11 17 2365, dated Oct. 17, 2011 (6 pages).

* cited by examiner

*Primary Examiner* — Doris Lee
(74) *Attorney, Agent, or Firm* — Buchanan Ingersoll & Rooney PC (57) ABSTRACT

An insulating tube for an electrode lead for medical use, particularly a cardiac pacemaker electrode lead, defibrillator electrode lead, electrode lead for nerve stimulation or the like, including a base material made of at least one material of the group consisting of silicones, polyurethanes, polyimide, PTFE, ETFE, and copolymers made of silicones and polyurethanes. In order to improve the functionality of such an insulating tube during friction of the tube with friction partners, at least in one volume region, which preferably forms the lateral surface of the insulating tube, the tube, in addition to the base material, includes a fibrous and/or particulate filler material having a higher abrasion resistance than the respective base material. A corresponding electrode lead is also provided, and a simple and cost-effective method for producing such an insulating tube and such an electrode lead.

11 Claims, 6 Drawing Sheets

ELECTRODE LEAD FOR MEDICAL USE, INSULATING TUBE AND METHOD FOR PRODUCING THE SAME

CROSS-REFERENCE TO RELATED APPLICATIONS

This patent application claims the benefit of U.S. Provisional Patent Application No. 61/366,529, filed on Jul. 22, 2010, which is hereby incorporated by reference in its entirety.

TECHNICAL FIELD

The present invention relates to an insulating tube for an electrode lead for medical use, in particular a cardiac pacemaker electrode lead, defibrillator electrode lead, electrode lead for nerve stimulation or the like, comprising a base material, such as silicone. The present invention further relates to such an electrode lead and to a method for producing an insulating tube for such an electrode lead, and further to a method for producing such an electrode lead.

BACKGROUND

Electronic medical systems such as, for example, cardiac pacemakers, defibrillators or neurological devices such as, for example, brain pacemakers for deep brain stimulation, spinal cord stimulation devices, TENS (Transcutaneous Electrical Nerve Stimulators) or devices for muscular stimulation therapy, and diagnostic devices analyzing the chemical properties of the patient's blood, other body parts or other body properties and parameters, frequently employ electrode leads, which are run in the patient's body and remain there at least for the period of the treatment or measurement. The electrode leads are connected in an electrically conductive manner to the optionally implantable electronic system.

These medical systems typically comprise a housing, which may be biocompatible, having an associated electronic circuit and an energy supply, such as, for example, a battery. The housing comprises at least one connection point to which the electrode lead or the electrode leads can be connected. The electrode lead or the electrode leads are used for transmitting the electric energy from the housing to the body part to be treated or analyzed, and vice versa.

To this end, the term "electrode lead" in medical technology denotes not only an element which is used to transmit electric energy according to the physical definition, but also comprises a lead having an electric conductor, together with the enveloping insulation thereof, which frequently is designed as an insulating tube, and all further functional elements which are rigidly connected to the lead. The electrode lead, for example, also comprises what is referred to as the electrode tip, by way of which the electric energy is introduced into the tissue to be treated. Frequently, an electrode tip is also provided with anchoring elements or retaining structures, which are used to ensure that the spatial position of the transition point of the electric energy in the tissue to be treated remains constant. The electrode tip, which forms a transition point of the electric energy into the tissue, can be designed as a recording, stimulating or working electrode.

In such electrode leads, an insulating hose made of silicone is frequently used to insulate the electrically conductive elements outside of the connection and electrode tip. Silicones have a high biocompatibility, sufficient hardness, and excellent permanently elastic properties.

For example, if an electrode lead chafes the collarbone of a person or a second electrode lead (for example, when a plurality of electrode leads are implanted), it is possible that the insulating tube is abraded so far that the functionality of the electrode lead is impaired.

For this reason, searches have been conducted for ways to increase the abrasion resistance of an insulating tube.

The published prior art DE 10 2008 010 188 A1, for example, proposed an insulation tube, wherein on the lateral surface of an inner, hollow-cylindrical layer a second layer is disposed, which comprises at least one polymer from the group consisting of polyurethane and silicone-polyurethane copolymer. The long-term stability of polyurethane, however, is not sufficient for many application purposes because the material degrades over time. In principle, degradation of the material also cannot be excluded for the therein proposed two-layer solution. In addition, such an electrode lead is considerably harder than a single-layer electrode lead having silicone insulation because of the arrangement of two layers on top of each other. This effect is particularly relevant for thin electrode leads. Furthermore, the concept of using an insulation tube made of two coaxially disposed layers is quite complex from a manufacturing engineering point of view.

Further, already known solutions relate to the development of new materials which combine the properties of silicone and polyurethane, such as the copolymers PurSil (silicone polyether urethane), CarboSil (polycarbonate urethane) or ElastEon®. These materials are so new that no long-term experience data is available yet. The use of these materials for medical applications is therefore also accordingly complex because of the extensive tests that are required.

The present invention is directed at overcoming one or more of the above-identified problems.

SUMMARY OF THE INVENTION

It is therefore an object of the present invention to provide an insulating tube and a corresponding electrode lead which exhibit improved abrasion behavior, without significantly impairing the biocompatibility or other mechanical properties. An object is further to provide simple and cost-effective methods for producing such an insulating tube and such an electrode lead.

The above object is achieved by an insulating tube, comprising a base material made of at least one material of the group consisting of silicones, polyurethanes, polyimide, PTFE, ETFE, and copolymers made of silicones and polyurethanes, wherein the insulating tube, in addition to being made of a base material, at least in one volume region, which preferably forms the lateral surface, comprises a particulate and/or fibrous filler material having a higher abrasion resistance than the respective base material that is used.

The filler material is preferably configured as sphere-, bean-, and/or grain-shaped particles and/or fibers, fiber sections or fiber mesh.

In order to produce an insulating tube according to the invention, for example, small filler particles or fiber sections are admixed to the extrudate and subsequently extruded into a tube or molded into a molding. Long fibers can be woven into the tube, for example. For this purpose, the fibers are woven around a tube inner part or a molding, which in turn is insert-molded again. Another possibility of weaving in fibers is to weave the fibers around a core, which is then insertmolded and/or extrusion-coated, wherein the core is later removed. A cross-mesh having fibers that are made of polyethylene terephthalate ("PET"), for example, and woven in a lattice-like manner around the lumen is particularly suited as the mesh. Further possibilities and details for producing an insulating tube according to the invention will be explained below.

The advantage of the insulating tube according to the invention is that the base material still considerably determines the properties of the insulating tube, such as the biocompatibility. However, abrasion during contact with a friction partner is stopped or lessened by the abrasion-resistant particles or fibers embedded in the base material matrix. Accordingly, the overall abrasion resistance can be considerably increased in an insulating tube according to the invention. The base material requires only minor adjustment with respect to elasticity and hardness for the overall material made of the base material and filler material to have the desired overall elasticity and overall hardness.

The present invention is therefore based on the realization that it is not necessary to change the entire material of the insulating tube in order to achieve the desired abrasion resistance. Rather, it is sufficient to replace only a small portion (for concentration information see below) of the material with an abrasion-resistant filler material. The particulate and/or fibrous filler material differs from the base material with respect to the phase or phase composition. This means that a spatial region is formed in a particle, or in a fiber, or in a fiber section, in which the determining physical parameters of the matter are different from the physical parameters of the matter of the base material. A particle, or a fiber, or a fiber section, preferably comprises a single phase, which is to say a spatial region that is homogeneous with respect to the physical parameters of the matter.

In the present invention, a silicone shall be understood as a poly(organo)siloxane, which is to say a polymer in which silicon atoms join together with oxygen atoms. Such a silicone may comprise molecule chains and/or networks. The remaining free valence electrons of the silicon are saturated with hydrocarbon groups. For the present medical application of an insulating tube, in particular, the following silicone rubbers may be used, preferably high temperature vulcanizing liquid silicone rubber (HTV LSR), which is extruded from a liquid (viscous) phase and cross-linked at high temperatures either induced by peroxide or catalyzed by platinum.

Advantageous materials which can form the filler material are at least one material of the group consisting of carbon, tantalum, platinum, gold, iridium, palladium, silicone derivatives, copolymers made of silicones, ceramic material, in particular silicon carbide, barium titanate, titanium dioxide, and zirconium dioxide, and thermoplastic material, in particular, polyurethane, polyamide, polyethylene, polyimide, PTFE (polytetrafluoroethylene), PFA (perfluoroalkoxy alkane), PET (polyethylene terephthalate), and ETFE (ethylene tetrafluoroethylene).

At this point, it should be expressly pointed out that when selecting materials from the stated groups for the base material and the filler material in order to implement the invention, materials having different abrasion resistances should always be selected, with the filler material having a higher abrasion resistance than the base material. This can be done by selecting different material classes, or by selecting different variants of the same, for example, polymer material class. When using different variants of one and the same material class for the base material and filler material, it is possible in some cases to achieve excellent bond strength between the materials of the base material and filler material. The filler material, for example, can be produced from previously cross-linked fibers made of more abrasion-resistant silicone. This filler material can then be admixed to the extrusion compound made primarily of silicone, wherein the filler material does not dissolve because it is already cross-linked.

The abrasion resistance can, in particular, be increased when the proportion of the filler material in the material of the insulating tube accounts for approximately 0.1% by volume to 30% by volume, and preferably approximately 1% by volume to 15% by volume. Filler material comprising very small particles or fibers (nano-material) is particularly preferably added in lower concentrations in the range of approximately 1% by volume to 5% by volume. As was already explained above, a small proportion of filler material having a higher abrasion resistance is already sufficient in order to significantly improve the properties of the insulating tube with respect to abrasion, without impairing the properties, such as biocompatibility, of the matrix base materials. At these concentrations, the electric insulation of the electrode lead by the insulating tube is also sufficiently ensured when using electrically conductive filler material.

In a further preferred embodiment, the diameter of the particulate filler material is approximately 1 nm to 100 nm, and preferably approximately 20 nm to 60 nm (nanoparticles). The diameter of the particulate filler material is determined, in particular, by measurement in the SEM (Scanning Electron Microscope). Smaller particles have the advantage that they can be used in smaller quantities for the same effect regarding abrasion resistance. Particularly in the second concentration range that is listed, the particles can still be processed well.

For the same reasons, the length of the fibrous filler material is approximately 0.1 mm to 10 mm in a further preferred embodiment. The length of the fibrous filler material is determined, in particular, by the desired resulting rigidity of the extruded or molded tube and constitutes the expansion of the fibers in the longitudinal direction. Particularly longer fibers advantageously increase the flexural strength of the insulating tube. In this respect, it is also advantageous if the length of the fibrous filler material is approximately 10 times to 100 times the fiber diameter.

Particularly good abrasion resistance results are achieved when the fibrous filler material is at least predominantly oriented such that the longitudinal direction of the fibers runs parallel to a longitudinal axis of the insulating tube. Here, the longitudinal direction of a fiber shall be understood as the direction of the respective fiber along which the fiber has the largest extension. The longitudinal orientation of the fibers results in axial interlocking of the protective layer obtained in this way. During flexural stress of the tube material, in this way a notch effect perpendicular to the tube axis, and consequently a risk of breakage, is counteracted. Radially disposed fibers can negatively influence the fatigue strength under reversed bending stresses of the insulating tube.

The filler material is preferably distributed unevenly over the cross-section of the insulating tube, for example, only in one layer or a partial layer or with a gradient. In the case of an uneven distribution of the filler material, specifically the regions of the insulating tube that are supposed to receive special protection against abrasion are provided with the filler material, for example, the regions in the vicinity of the outer lateral surface of the insulating tube and/or in the vicinity of the inner wall of the opening(s) in the insulating tube in which the conductor elements are disposed.

The above object is achieved, with the advantages described above, by an electrode lead which comprises an insulating tube having the properties stated above, wherein the insulating tube, in one section of the electrode lead in which the tube is disposed, preferably forms the outer surface of the electrode lead or surrounds the electrode on the outside.

The insulating tube insulates the inner electrically conductive elements of the electrode lead to the outside and additionally offers protection against mechanical friction with a friction partner.

A simple and cost-effective method for producing an insulating tube according to the invention comprises the following steps:

Preparing at least one first base material made of at least one material of the group consisting of silicones, polyurethanes, polyimide, PTFE, ETFE, and copolymers made of silicons and polyurethanes, as well as a particulate and/or fibrous filler material, wherein the filler material has a higher abrasion resistance than the first base material, mixing the first base material and the filler material, shaping the single- or multi-layer insulating tube by
  extruding or molding the mixture comprising the first base material and the filler material into a single-layer insulating tube, or
  coextruding the mixture comprising the first base material and the filler material together with at least one second base material made of at least one material of the group consisting of silicones, polyurethanes, polyimide, PTFE, ETFE, and copolymers made of silicones and polyurethanes, into an at least double-layer insulating tube, or
  extruding, one time or multiple times, the mixture comprising the first base material and the filler material onto a tube comprising at least one second base material made of at least one material of the group consisting of silicones, polyurethanes, polyimide, PTFE, ETFE, and copolymers made of silicones and polyurethanes, into an at least double-layer insulating tube, or
  molding, one time or multiple times, the mixture comprising the first base material and the filler material around a tube comprising at least one second base material made of at least one material of the group consisting of silicones, polyurethanes, polyimide, PTFE, ETFE, and copolymers made of silicones and polyurethanes, into an at least double-layer insulating tube, or
  dipping, one time or multiple times, a tube comprising at least one second base material made of at least one material of the group consisting of silicones, polyurethanes, polyimide, PTFE, ETFE, and copolymers made of silicones and polyurethanes, into a mixture made of the liquid first base material and the filler material so as to create an at least double-layer insulating tube,
    wherein on the at least double-layer insulating tube the layer made of the first base material comprising the filler material is preferably disposed such that it forms the outer lateral surface of the insulating tube.

In a particularly preferred exemplary embodiment, a tube comprising the second base material is dipped into low-viscosity silicone (particularly and preferably RTV silicone), to which the filler material stated above has been added.

A further cost-effective method for producing an insulating tube according to the invention comprises the following steps:

Preparing at least one fiber-reinforced first base material made of at least one material of the group consisting of silicones, polyurethanes, polyimide, PTFE, ETFE, and copolymers made of silicones and polyurethanes, wherein the material of the fibers has a higher abrasion resistance than the first base material, shaping the single- or multi-layer insulating tube by
  extruding the fiber-reinforced first base material into a single-layer insulating tube, or
  coextruding the fiber-reinforced first base material together with at least one second base material made of at least one material of the group consisting of silicones, polyurethanes, polyimide, PTFE, ETFE, and copolymers made of silicones and polyurethanes, into an at least double-layer insulating tube, or
  extruding, one time or multiple times, the fiber-reinforced first base material onto a tube comprising at least one second base material made of at least one material of the group consisting of silicones, polyurethanes, polyimide, PTFE, ETFE, and copolymers made of silicones and polyurethanes, into an at least double-layer insulating tube, or
  molding, one time or multiple times, the fiber-reinforced first base material around a tube comprising at least one second base material made of at least one material of the group consisting of silicones, polyurethanes, polyimide, PTFE, ETFE, and copolymers made of silicones and polyurethanes, into an at least double-layer insulating tube, or
  dipping, one time or multiple times, a tube comprising at least one second base material made of at least one material of the group consisting of silicones, polyurethanes, polyimide, PTFE, ETFE, and copolymers made of silicones and polyurethanes, into a liquid fiber-reinforced first base material so as to create an at least double-layer insulating tube,
    wherein on the at least double-layer insulating tube the layer made of the fiber-reinforced first base material is preferably disposed such that it forms the outer lateral surface of the insulating tube.

When using a fiber mesh, the following cost-effective method for producing an insulating tube according to the invention can be employed:

Preparing a fiber mesh and a first base material made of at least one material of the group consisting of silicones, polyurethanes, Polyimide, PTFE, ETFE, and copolymers made of silicons and polyurethanes, wherein the material of the fibers has a higher abrasion resistance than the first base material, applying the fiber mesh onto a core or onto a tube comprising at least one second base material made of at least one material of the group consisting of silicones, polyurethanes, polyimide, PTFE, ETFE, and copolymers made of silicones and polyurethanes, or a molding comprising at least one second base material made of at least one material of the group consisting of silicones, polyurethanes, polyimide, PTFE, ETFE, and copolymers made of silicones and polyurethanes, shaping the single- or multi-layer insulating tube by
  extruding, one time or multiple times, the first base material onto the fiber mesh, or
  molding, one time or multiple times, the first base material around the fiber mesh, or
  dipping, one time or multiple times, the fiber mesh or the fiber mesh with the tube or with the molding into at least the liquid first base material, wherein optionally the core is subsequently removed.

Advantageous materials which can form the filler material, this being the particles or fibers, are at least one material of the group consisting of carbon, tantalum, platinum, gold, iridium, palladium, ceramic material, in particular silicon carbide, barium titanate, titanium dioxide, and zirconium dioxide, and thermoplastic material, in particular polyurethane, polyamide, polyethylene, polyimide, PTFE (polytetrafluoroethylene), PFA (perfluoroalkoxy alkane), PET (polyethylene terephthalate), and ETFE (ethylene tetrafluoroethylene).

Extrusion and coextrusion are simple methods for producing an insulating tube having increased abrasion resistance that are easy to control. These methods further have the advantage that the layer thickness and the concentration of the filler material in the respective layer can be easily and individually adjusted. In addition, thorough mixing of the silicone base material and the filler material can be achieved in the respective layer.

The above object is further achieved by a method for producing an electrode lead, wherein an insulating tube is produced as described above and subsequently the insulating tube is disposed on and/or around a conductor element such that it surrounds the same on the outside. The insulating tube is used both to electrically insulate the conductor element and to protect the same mechanically against abrasion. In particular because of the advantages described above, this production method is also a simple and cost-effective method for producing the insulating tube.

Further objectives, characteristics, advantages, and application possibilities of the invention will be apparent from the following description of exemplary embodiments, the figures, and the appended claims. All characteristics described and/or illustrated, either alone or in any arbitrary combination, form the subject matter of the invention, independently of their combination in the claims or dependent claims.

DETAILED DESCRIPTION

Figure 1:
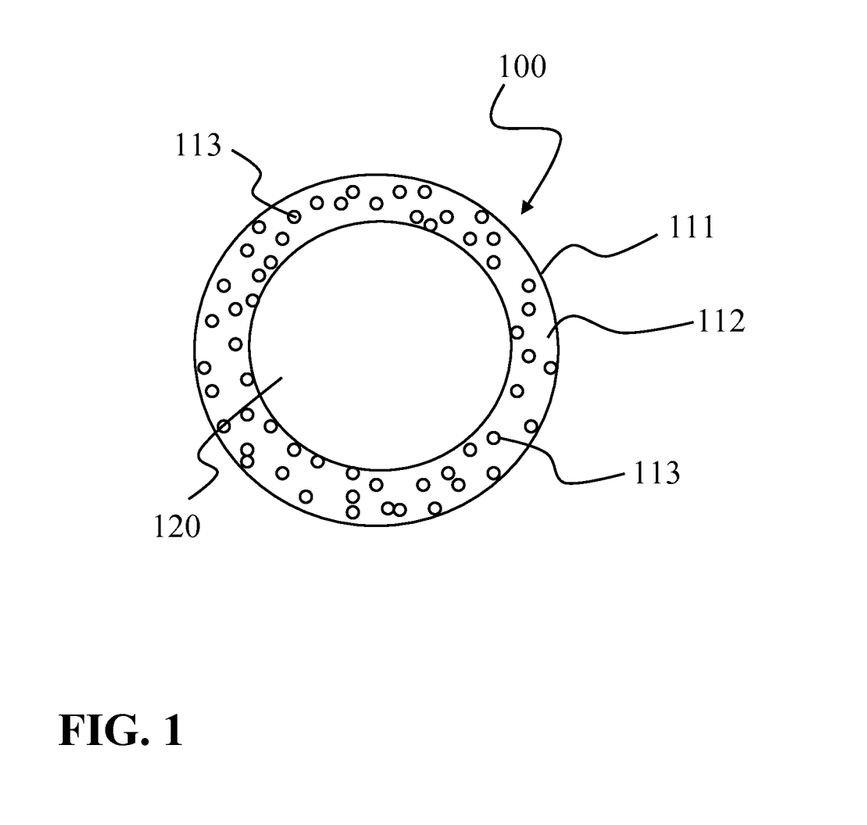
FIG. 1 is a cross-section of a first exemplary embodiment of an insulating tube according to the invention.

The insulating tube 100 illustrated in FIG. 1 comprises only a single layer 111, which has a substantially hollow-cylindrical design. The layer 111 is comprised of a base material matrix 112 made of, for example, LSR (liquid silicone rubber), in which the sphere-shaped particles 113, made of, for example, barium titanate, as the filler material are embedded. Such barium titanate particles 113 have an average diameter of approximately 2 µm. As an alternative or in addition, it is also possible to embed tantalum particles as the filler material into the base material matrix. Tantalum particles have an average diameter of approximately 40 µm. The continuous cylindrical opening 120 of the insulating tube 100 is used to accommodate the conductive elements, which at the distal end of the electrode lead form the electrode or electrodes, and at the proximal end form a connecting element for the electrically conductive connection to an electronic system. Both the barium titanate particles and/or the tantalum particles 113 have a higher abrasion resistance than the base material LSR 112.

Figure 2:
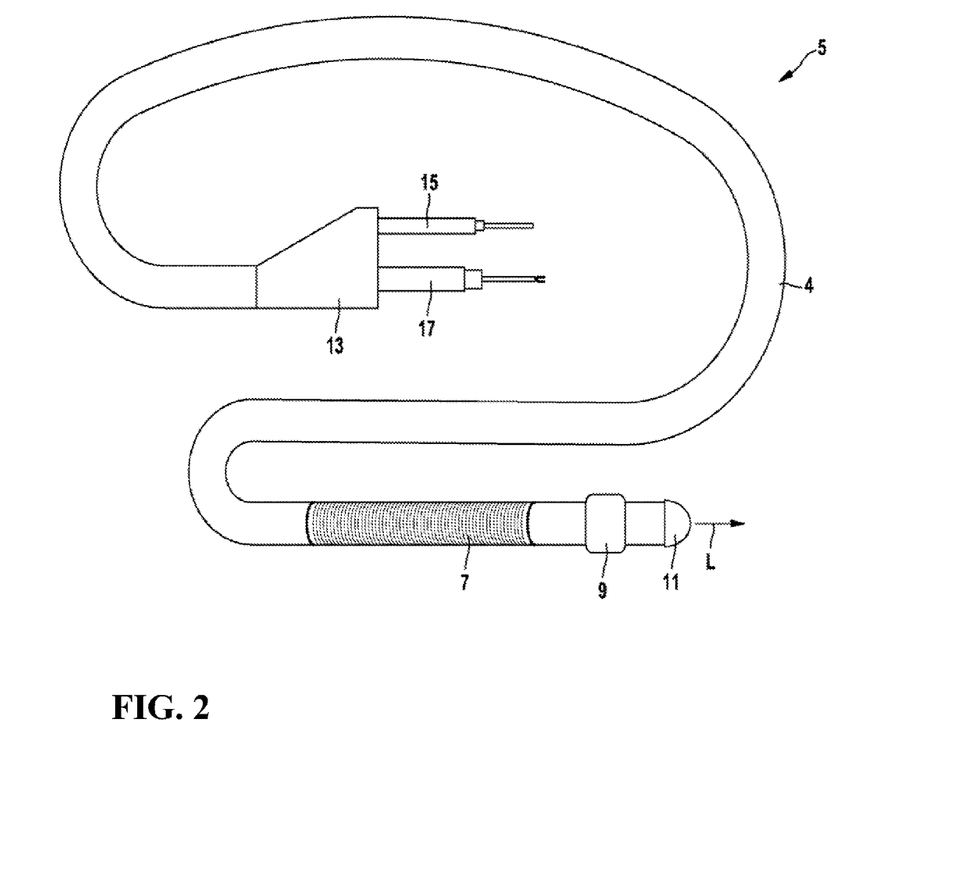
FIG. 2 is a side view of an exemplary embodiment of an electrode lead according to the invention.

FIG. 2 shows the use of such an insulating tube 100 by way of the example of an implantable shock electrode lead 5, which is inserted in a defibrillator. In FIG. 2, the reference numeral 4 denotes the insulating tube. The design thereof can be analogous to the insulating tube 100 illustrated in FIG. 1, or analogous to one of the exemplary embodiments described below. The electrode lead 5 has a proximal end and a distal end in the longitudinal direction L. At the distal end, the shock electrode lead 5 has an elongated electrode 7, which is run, for example, with wall contact in the heart of a patient, as well as an annular electrode 9 and a tip electrode 11, which are provided for sensing and/or stimulating purposes. At the proximal end of the shock electrode lead 5, plug elements 15, 17 are provided, which extend out of a Y-distributor 13 and are associated with the electrode 7 and the stimulation or detection electrodes 9, 11 and which are used for the electrical connection to an implantable device (not illustrated).

Figure 3:
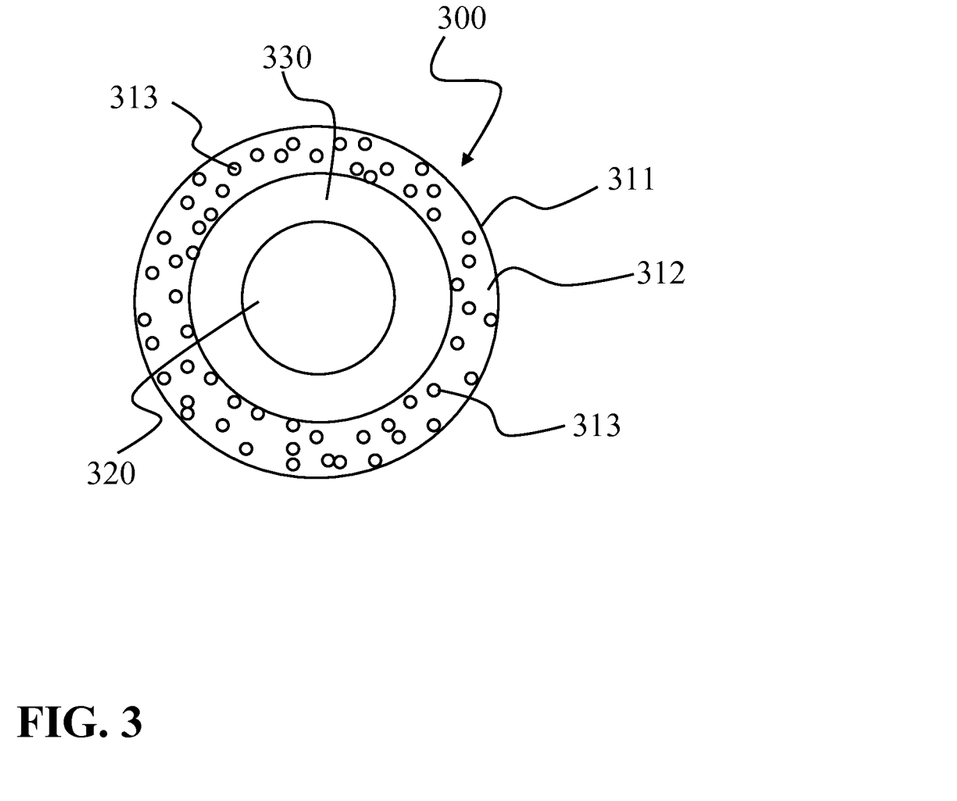
FIG. 3 is a cross-section of a second exemplary embodiment of an insulating tube according to the invention.

In the second exemplary embodiment illustrated in FIG. 3, the insulating tube 300 is comprised of two layers. The inner layer 330, which is designed in a substantially hollow-cylindrical manner having a continuous opening 320 in order to accommodate the conductive elements, is made of, for example, LSR. A second layer 311 is disposed concentrically to the inner layer 320 on the outer surface (lateral surface) of the inner layer 320 and, analogous to the first exemplary embodiment of the insulating tube, has an LSR base material matrix 312 and particles 313 made of, for example, barium titanate which have an average diameter of approximately 2 µm.

Figure 4:
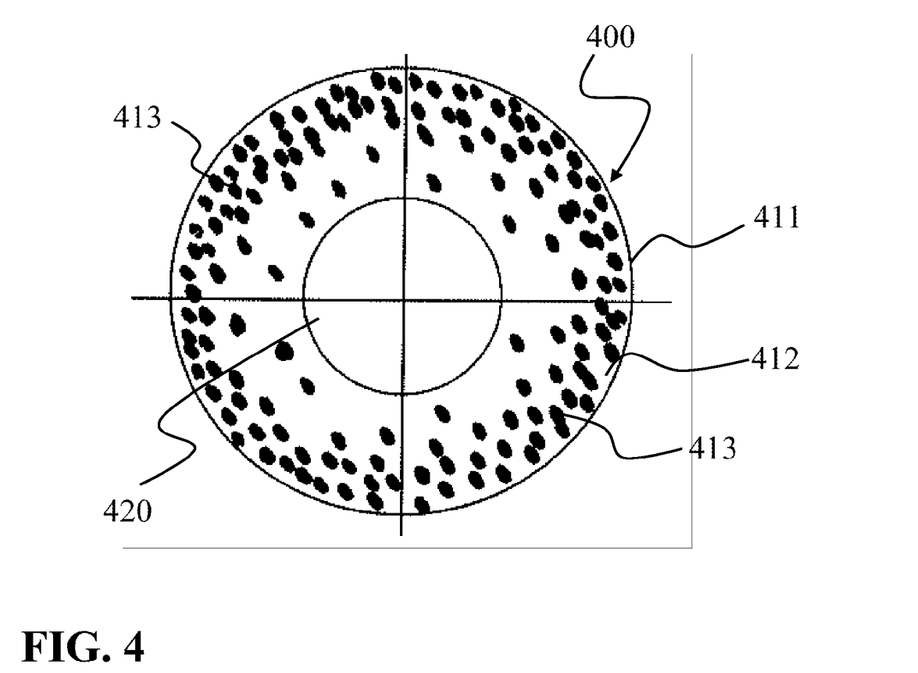
FIG. 4 is a cross-section of a third exemplary embodiment of an insulating tube according to the invention.

The design of the insulating tube 400 illustrated in FIG. 4 corresponds substantially to the insulating tube 100 shown in FIG. 1, wherein here the barium titanate particles 413 are distributed unevenly over the cross-section. The concentration of the barium titanate particles 413 increases from the inside to the outside. This has the advantage that a higher abrasion resistance is achieved in the outer region of the cross-section so as to protect the insulating tube 400, primarily against external friction.

In contrast, in the exemplary embodiments illustrated in FIGS. 1 and 2, the abrasion-resistant particles 113, 313 in the respective layers 111, 311 are distributed evenly over the cross-section of the respective layer 111, 311.

Figure 5:
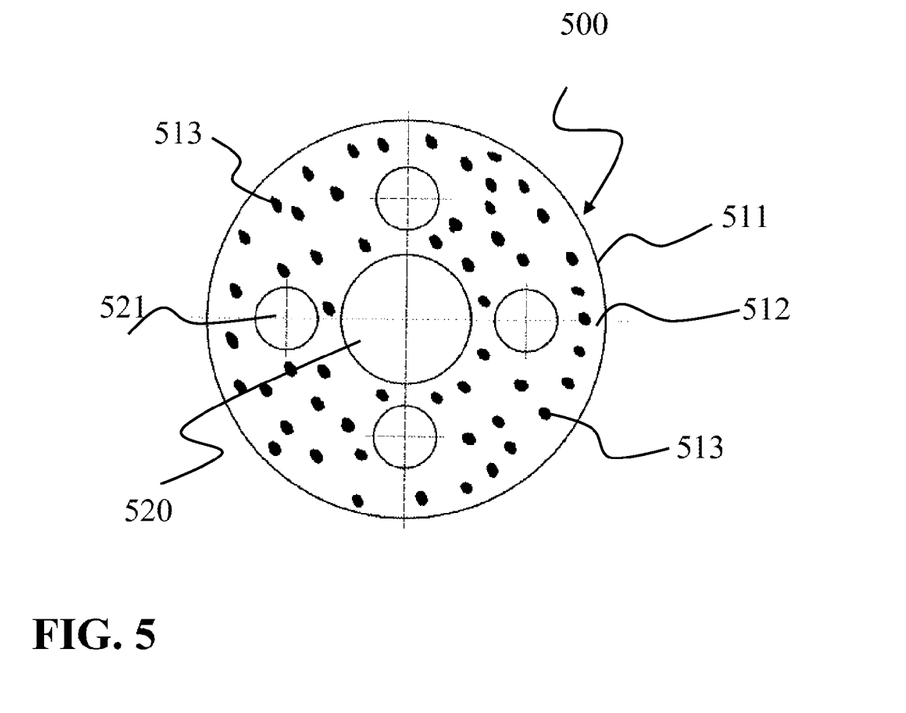
FIG. 5 is a cross-section of a fourth exemplary embodiment of an insulating tube according to the invention.

Analogous to the exemplary embodiments illustrated in FIGS. 1 and 3, the fourth exemplary embodiment of an insulating tube 500 illustrated in FIG. 5 shows an even distribution of the barium titanate particles 513 over the cross-section of the layer 511. In addition to a central, continuous, substantially cylindrical opening 520, the insulating tube comprises four additional continuous, substantially cylindrical openings 521, which are disposed evenly distributed around the central opening 520. The centers of the cross-sections of the openings 521 are disposed approximately on a circle, and in each case offset by approximately 90°. The cross-section of each opening 521 has a smaller diameter than the cross-section of the central opening 520. When used for an electrode lead, the openings 520, 521 can optionally be equipped with spiral or cable feed lines.

Figure 6:
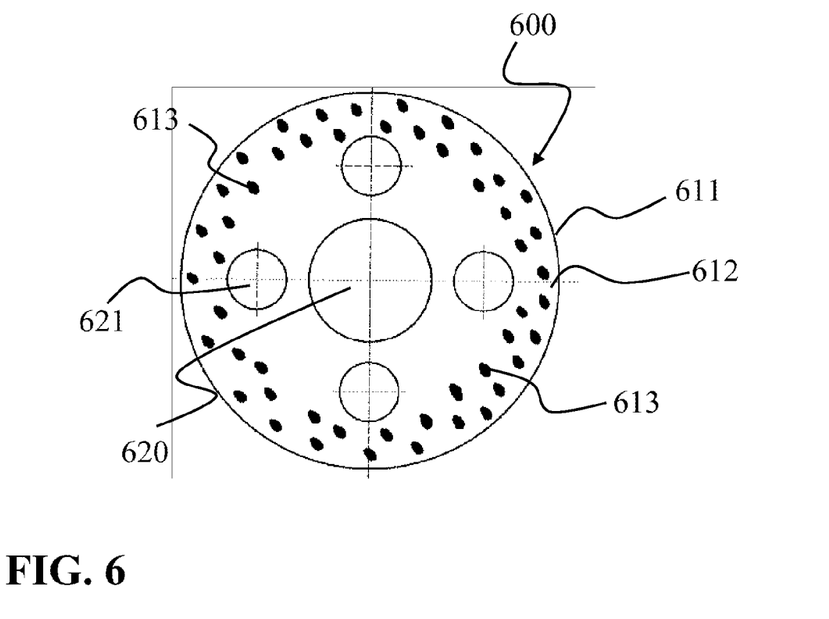
FIG. 6 is a cross-section of a fifth exemplary embodiment of an insulating tube according to the invention.
Figure 7:
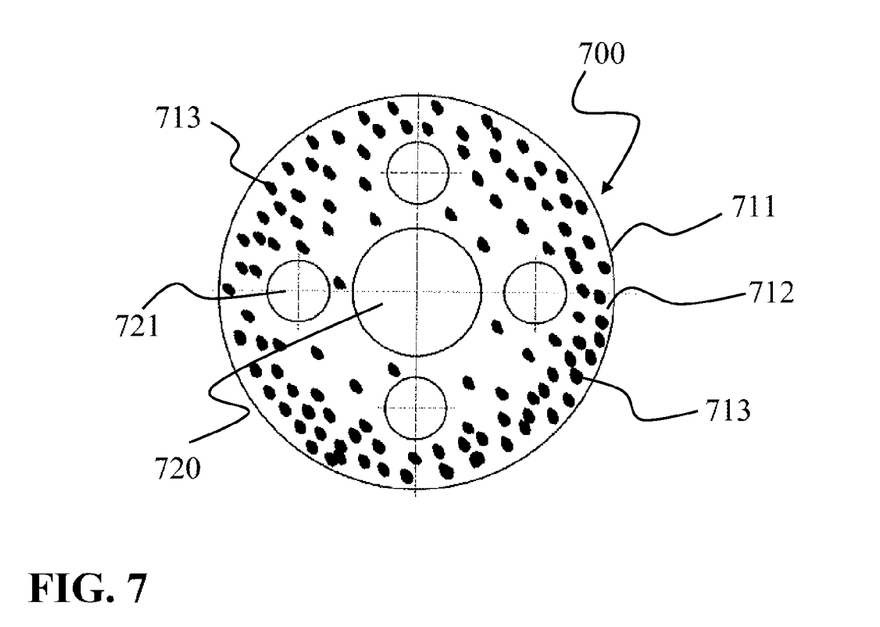
FIG. 7 is a cross-section of a sixth exemplary embodiment of an insulating tube according to the invention.

The exemplary embodiment of an insulating tube 700 illustrated in FIG. 7 corresponds substantially to the embodiment illustrated in FIG. 5, with the exception of the distribution of the barium titanate particles 713. The particles 713 are not evenly distributed over the cross-section in the insulating tube 700, but the concentration thereof in the layer 711 increases from the inside to the outside, which is to say, the concentration of the particles 713 has a gradient. In the exemplary embodiment of an insulating tube 600 illustrated in FIG. 6, the distribution of the barium titanate particles 613 is likewise uneven, wherein here the barium titanate particles 613 are disposed substantially close to the outer lateral surface of the layer 611 in an outer partial layer. The concentration of the barium titanate particles 613 therefore does not increase gradually, but rather suddenly in the direction of the outer lateral surface of the layer 611.

Figure 8:
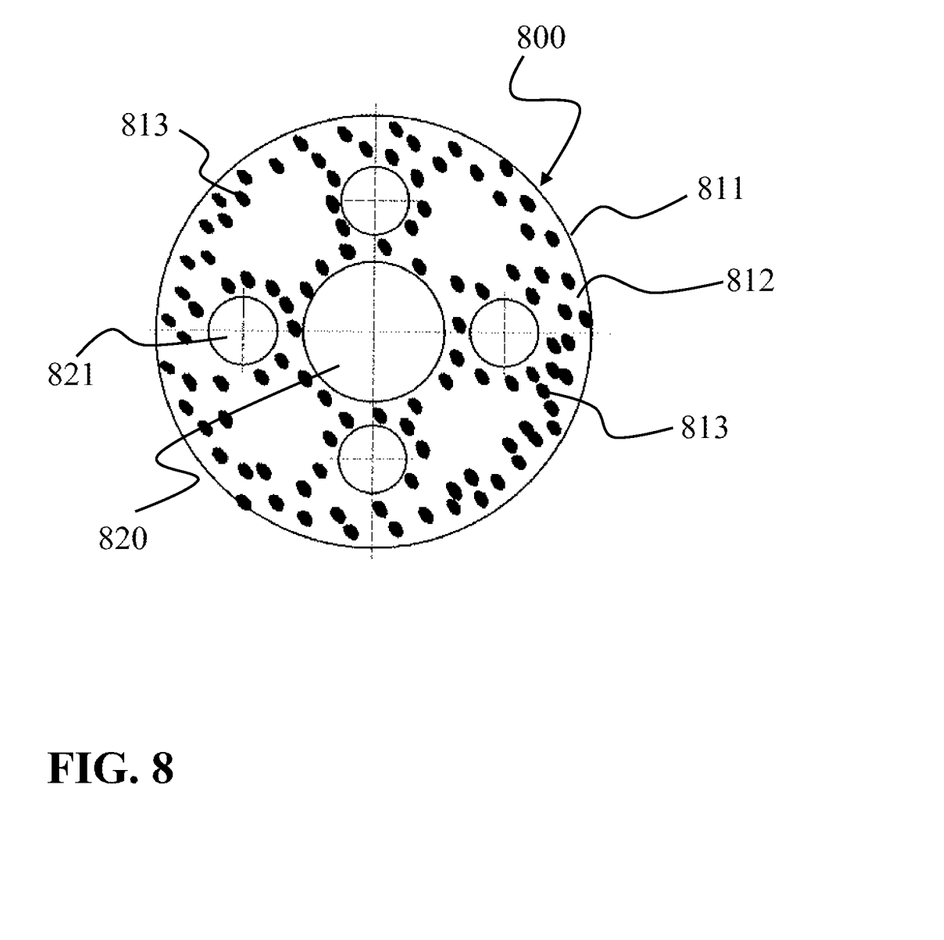
FIG. 8 is a cross-section of a seventh exemplary embodiment of an insulating tube according to the invention.

In the exemplary embodiment of an insulating tube 800 illustrated in FIG. 8, the abrasion-resistant barium titanate particles 813 are also unevenly distributed. The particles 813 can be found substantially in partial layers of the layer 811, which form the outer lateral surface and the inner surfaces formed by the openings 820, 821. In this way, in particular the abrasion resistance to friction partners disposed in the openings 820, 821 is increased. In this exemplary embodiment as well, the concentration of the barium titanate particles 813 increases rather suddenly in the vicinity of the outer lateral surface and the inner surfaces of the openings 820, 821.

The insulating tubes 400, 600, 700, 800, each having the uneven distribution of the particles, can be produced by coextrusion, for example, specifically in that two materials are extruded simultaneously, of which only one is mixed with the filler material. As an alternative, the uneven distributions can be generated by way of extrusion coating, wherein the first layer is pre-crosslinked. The variant in which the filler material is disposed at the walls (e.g., insulating tube 800) could be achieved by admixing filler material (particularly nano-particles) into the air current required for maintaining the lumen. Optionally, the effect can be improved by a static charge of the particles.

An insulating tube according to the exemplary embodiment illustrated in FIG. 1 was produced using various filler materials having increased abrasion resistance, analyzed by way of an abrasion test, and compared to an insulating tube which contained no filler material having increased abrasion resistance. The first table below shows the results of an abrasion test for the abrasion on a rough metal surface chafing the insulating tube. During the abrasion test, the tube is pressed onto a rotating grinding body (in this case metal, for example) having a defined roughness, in this case a roughness of Rz 6.3, for example, using a defined force (in this case 4 N, for example). The distance that the grinding body travels (expressed in the number of revolutions) in relation to the material that is abraded is a measure of the abrasion resistance of the tube, which can be compared among each other if the tube geometries are identical. In the following example, the friction travel is the distance that the grinding body traveled at the defined force and the defined roughness of the grinding body, which is required to achieve abrasion of 0.3 mm.

| Base material | Filler material having increased abrasion resistance | Proportion (in % by volume)/ particle size | Friction travel of the metallic abrasion partner (roughness Rz 6.3/ force 4 N) | Abrasion resistance (factor) |
| --- | --- | --- | --- | --- |
| Silicone tube made of LSR, having a | — | 0% | 20 m | 1 |

-continued

| Base material | Filler material having increased abrasion resistance | Proportion (in % by volume)/ particle size | Friction travel of the metallic abrasion partner (roughness Rz 6.3/ force 4 N) | Abrasion resistance (factor) |
| --- | --- | --- | --- | --- |
| Shore hardness of 50 Silicone tube made of LSR, having a Shore hardness of 50 | Barium titanate | 15%/3 μm | 60 m | 3 |
| Silicone tube made of LSR, having a Shore hardness of 50 | Tantalum | 15%/44 μm | 100 m | 5 |

The results shown above demonstrate that the abrasion behavior of a silicone insulating tube comprising the stated filler material is considerably improved compared to a silicone insulating tube having no filler material for an abrasion partner made of metal having a defined roughness. Such an improvement is already achieved by a small addition of only 15% by volume.

In order to produce an insulating tube having an electrode lead, the filler material is added to a base material extrudate and carefully mixed before it is extruded into a tube using a conventional extruder for high temperature vulcanizing materials. A multi-turn helix is inserted into this tube as the electrode feed line and fixed at the ends by way of adhesive (glue).

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

| List of reference numerals: | |
| --- | --- |
| 4, 100, 300, 400, 500, 600, 700, 800 | Insulating tube |
| 5 | Shock electrode lead |
| 7 | Electrode |
| 9 | Annular electrode |
| 11 | Tip electrode |
| 13 | Y-distributor |
| 15, 17 | Plug element |
| 111, 311, 411, 511, 611, 711, 811 | Layer |
| 112, 312, 412, 512, 612, 712, 812 | Base material |
| 113, 313, 413, 513, 613, 713, 813 | Particle |
| 120, 320, 420, 520, 620, 720, 820 | Opening |
| 521, 621, 721, 821 | Opening |
| 330 | Layer |
| L | Longitudinal direction of the shock electrode lead 5 |

We claim:

1. An insulating tube for an electrode lead for medical use, comprising a base material made of at least one material of the group consisting of silicones, polyurethanes, polyimide, PTFE, ETFE, and copolymers made of silicones and polyurethanes, wherein at least in a volume region, which forms the lateral surface of the insulating tube, the insulating tube, in addition to the base material, comprises a fibrous filler material having a higher abrasion resistance than the respective base material, wherein the fibrous filler material is at least predominately oriented such that the longitudinal direction of the fibers runs parallel to a longitudinal axis of the insulating tube.

2. The insulating tube according to claim 1, wherein the filler material comprises at least one material of the group consisting of carbon, tantalum, platinum, gold, iridium, palladium, silicone derivatives, copolymers made of silicones, ceramic material, silicon carbide, barium titanate, zirconium dioxide, thermoplastic material, polyurethane, polyamide, polyethylene, polyimide, PET, PFA, PTFE and ETFE.

3. The insulating tube according to claim 1, wherein the proportion of the filler material in the material of the insulating tube accounts for 0.1% by volume to 30% by volume.

4. The insulating tube according to claim 1, wherein the proportion of the filler material in the material of the insulating tube accounts for 1% by volume to 15% by volume.

5. The insulating tube according to claim 1, wherein the filler material is configured as fibers, fiber sections and/or fiber mesh.

6. The insulating tube according to claim 1, wherein the diameter of the filler material is 1 nm to 100 nm.

7. The insulating tube according to claim 1, wherein the diameter of the filler material is 20 nm to 60 nm.

8. The insulating tube according to claim 1, wherein the length of the fibrous filler material is 0.1 mm to 10 mm.

9. The insulating tube according to claim 1, wherein the filler material is distributed unevenly over the cross-section of the insulating tube.

10. The insulating tube according to claim 1, wherein a concentration of the fibrous filler material increases from an inside to an outside of the insulating tube.

11. An electrode lead for medical use, comprising the insulating tube according to claim 1, wherein the insulating tube surrounds the electrode on the outside in the section of the electrode lead in which the tube is disposed along the same.

* * * * *